(12) United States Patent
Becker et al.

(10) Patent No.: US 8,874,197 B2
(45) Date of Patent: Oct. 28, 2014

(54) RISK DETERMINATION FOR VENTRICULAR ARRHYTHMIA

(71) Applicant: Medtronic, Inc.

(72) Inventors: Daniel Becker, Heerlen (NL); Raphael Schneider, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/664,017

(22) Filed: Oct. 30, 2012

(65) Prior Publication Data

US 2014/0121542 A1    May 1, 2014

(51) Int. Cl.
*A61B 5/0472*    (2006.01)
*A61B 5/0452*    (2006.01)

(52) U.S. Cl.
CPC .............. *A61B 5/0472* (2013.01); *A61B 5/0452* (2013.01)
USPC ............................. 600/513; 600/509; 600/515

(58) Field of Classification Search
CPC ............... A61B 5/0452; A61B 5/0402; A61B 5/04012; A61B 5/0006; A61B 5/0456; A61B 5/0205; A61B 5/04525; A61B 5/0468; A61B 5/046; A61N 1/36585
USPC .......................... 600/509, 513, 515, 516, 517
See application file for complete search history.

(56) References Cited

U.S. PATENT DOCUMENTS

| 5,092,340 A | 3/1992 | Yamaguchi et al. |
| 5,306,293 A | 4/1994 | Zacouto |
| 2010/0217144 A1 | 8/2010 | Brian |
| 2010/0274141 A1 | 10/2010 | Patangay et al. |
| 2010/0274147 A1* | 10/2010 | Patangay et al. .............. 600/515 |
| 2011/0087121 A1 | 4/2011 | Zhang et al. |
| 2012/0190957 A1* | 7/2012 | Gill et al. ....................... 600/374 |

FOREIGN PATENT DOCUMENTS

| CN | 102 138 789 A | 8/2011 |
| KR | 2012 0116213 A | 10/2012 |

OTHER PUBLICATIONS

P0037065.WOU2 (PCT/US2013/066175) PCT Notification of Transmittal of the International Search Report and the Written Opinion of the International Searching Authority.
"Methods derived from nonlinear dynamics for analyzing heart rate variability", by Andreas Voss et al., Philosophical Transactions of The Royal Society, vol. 367, No. 1887, Jan. 28, 2009, pp. 277-296.

* cited by examiner

*Primary Examiner* — Christopher D Koharski
*Assistant Examiner* — Michael Carey
(74) *Attorney, Agent, or Firm* — Michael C. Soldner

(57) ABSTRACT

Risk determination for a near fatal ventricular arrhythmia of a patient. An electrocardiogram of a heart of the patient is obtained. A parameter is measured, using an electrocardiogram of a heart of the patient, indicative of an autonomic nervous system of the patient. A numeric score is assigned for the parameter indicative of the conduction system of the heart. A numeric score is assigned for the parameter indicative of the autonomic nervous system. A ratio of the numeric score of the parameter indicative of the conduction system of the heart of the patient and the numeric score of the parameter indicative of the autonomic nervous system of the patient is calculated. The risk of the potentially near fatal ventricular arrhythmia of the patient is determined to be significant if the ratio is greater than a predetermined threshold. An action responsive to the determining step is taken.

34 Claims, 3 Drawing Sheets

RISK DETERMINATION FOR VENTRICULAR ARRHYTHMIA

FIELD

The present invention relates generally to risk determination for ventricular arrhythmia and, more particularly, to devices and methods for determining the risk for near fatal ventricular arrhythmia of a patient.

BACKGROUND

Ventricular arrhythmias are dangerous and are particularly dangerous in post myocardial infarction patients. Ventricular arrhythmias are sometimes defined as abnormal rapid heart rhythms (arrhythmias) that originate in the lower chambers of the heart (the ventricles). Ventricular arrhythmias include ventricular tachycardia and ventricular fibrillation. Both are life threatening arrhythmias most commonly associated with heart attacks or scarring of the heart muscle from previous heart attack.

Ventricular arrhythmias are potentially lethal in acute myocardial infarction patients leading to deaths of as many as six percent (6%) of acute myocardial infarction patients in the first year.

An indication of a patient's relative risk of developing a ventricular arrhythmia would allow one to manage the hazard going forward. An indication of relatively high risk for a patient developing a ventricular arrhythmia could typically lead to patient management, sometimes immediate patient management, diagnosis and perhaps eventually to implantable cardioversion defibrillator or implantable pacemakers.

SUMMARY

The apparatus and method described herein allow the early warning or prognosis of potentially near fatal ventricular arrhythmias and can be useful, for example, in acute phase myocardial infarction patients.

The apparatus and method rely on measurements such as QRS-width to assess how the local conduction system in the heart works and a measurement of a parameter of the global autonomic nervous system and assigns a numeric score for each one. A numeric risk score can be calculated either continuously in an implanted device or in an external device receiving EGM/ECG data from an implanted device. Based on the risk score, an action is taken, for example an alarm is activated, when the risk score goes above a predetermined threshold. Alternatively, medical device settings and/or therapies are instituted or modified or other medical devices utilized to mitigate the risk as appropriate.

In an embodiment, an apparatus determines a risk of a potentially near fatal ventricular arrhythmia of a patient. An implantable medical device is configured to obtain an electrocardiogram of a heart of the patient, measure; using the electrocardiogram, a parameter indicative of a conduction system of the heart of the patient; and measure, using the electrocardiogram, a parameter indicative of an autonomic nervous system of the patient. The system is configured to assign a numeric score for the parameter indicative of the conduction system of the heart of the patient; calculate a ratio of the numeric score of the parameter indicative of the conduction system of the heart of the patient with the numeric score of the parameter indicative of the autonomic nervous system of the patient; and take an action responsive to the risk of the potentially near fatal ventricular arrhythmia of the patient being significant if the ratio is greater than a predetermined threshold.

In an embodiment, a device implemented method determines a risk of a potentially near fatal ventricular arrhythmia of a patient. A medical device is implanted in the patient and configured to obtain an electrocardiogram of a heart of the patient. A parameter is measured, using the electrocardiogram, indicative of the local conduction system of the patient. A parameter is measured, using the electrocardiogram, indicative of an autonomic nervous system of the patient. A numeric score is assigned for the parameter indicative of the conduction system of the heart of the patient. A numeric score is assigned for the parameter indicative of the autonomic nervous system of the patient. A ratio of the numeric score of the parameter indicative of the conduction system of the heart of the patient and the numeric score of the parameter indicative of the autonomic nervous system of the patient is calculated. The risk of the potentially near fatal ventricular arrhythmia of the patient is determined to be significant if the ratio is greater than a predetermined threshold. An action responsive to the determining step is taken.

In an embodiment, an alarm is activated.

In an embodiment, a therapeutic action with the patient is administered.

In an embodiment, a cardiac device is implanted and operatively coupled to the medical device. The cardiac device is configured to perform a therapeutic action for the patient in response to the risk of the potentially near fatal ventricular arrhythmia.

In an embodiment, the cardiac device is a cardiac pacemaker.

In an embodiment, the medical device is at least one of a cardioverter and a cardiac rhythm therapy device.

In an embodiment, the parameter indicative of a conduction system of the heart of the patient is a QRS-width.

In an embodiment, the numeric score of the QRS-width is scored in time.

In an embodiment, the numeric score of the QRS-width is scored in milliseconds.

In an embodiment, the parameter indicative of the autonomic nervous system is a detrended fluctuation analysis slope Alpha-1 (DFa1).

In an embodiment, the period of time is at least ten (10) hours.

In an embodiment, a higher value of the numeric score for the parameter indicative of the conduction system of the heart of the patient is indicative of a greater risk of the potentially near fatal ventricular arrhythmia of the patient.

In an embodiment, a lower value of the parameter indicative of the autonomic nervous system of the patient is indicative of a greater risk of the potentially near fatal ventricular arrhythmia of the patient.

In an embodiment, the numeric score of the detrended fluctuation analysis slope Alpha-1 (DFa1) is scored in slope value.

In an embodiment, the parameter indicative of a conduction system of the heart and the parameter indicative of an autonomic nervous system of the patient step are both measured over a period of time.

In an embodiment, the threshold indicative of the risk of the potentially near fatal ventricular arrhythmia of the patient is one hundred thirty-five (135).

In an embodiment, the patient is a post myocardial infarction patient.

FIGURES

DESCRIPTION

The system and method allows the early warning or prognosis of potentially near fatal ventricular arrhythmias such as ventricular arrhythmias found in acute phase myocardial infarction patients.

As noted, ventricular arrhythmias are potentially lethal in acute myocardial infarction patients leading to deaths of as many as six percent (6%) of acute myocardial infarction patients in the first year. An embodiment provides an indication of a patient's relative risk of developing a ventricular arrhythmia which would allow one to manage the hazard going forward. An indication of relatively high risk for a patient developing a ventricular arrhythmia could typically lead to patient management, sometimes immediate patient management, diagnosis and perhaps eventually to implantable cardioversion defibrillator or implantable pacemakers.

The system and method first measures (1) QRS-width to assess how the local conduction system in the heart works and (2) assesses the status of the global autonomic system, for example by measuring the detrended fluctuation analysis slope Alpha-1 (DFa1). A numeric risk score is calculated from numeric values of both factors. For example, the numeric risk equals the ratio of QRS-width to DFa1. Risk scores of greater than or equal to 135 are seen as pathologic. The risk score can either be calculated continuously in an implanted device, e.g., an implantable loop recorder, or in an external device receiving EGM/ECG data from an implanted device.

Based on the risk score, an action is taken, for example an alarm is activated, when the risk score goes above a predetermined threshold. Alternatively, medical device settings and/or therapies are instituted or modified or other medical devices utilized to mitigate the risk as appropriate.

It is to be recognized and understood that the risk can be combined or supplemented with other clinical data to refine the risk of the patient.

Figure 1:
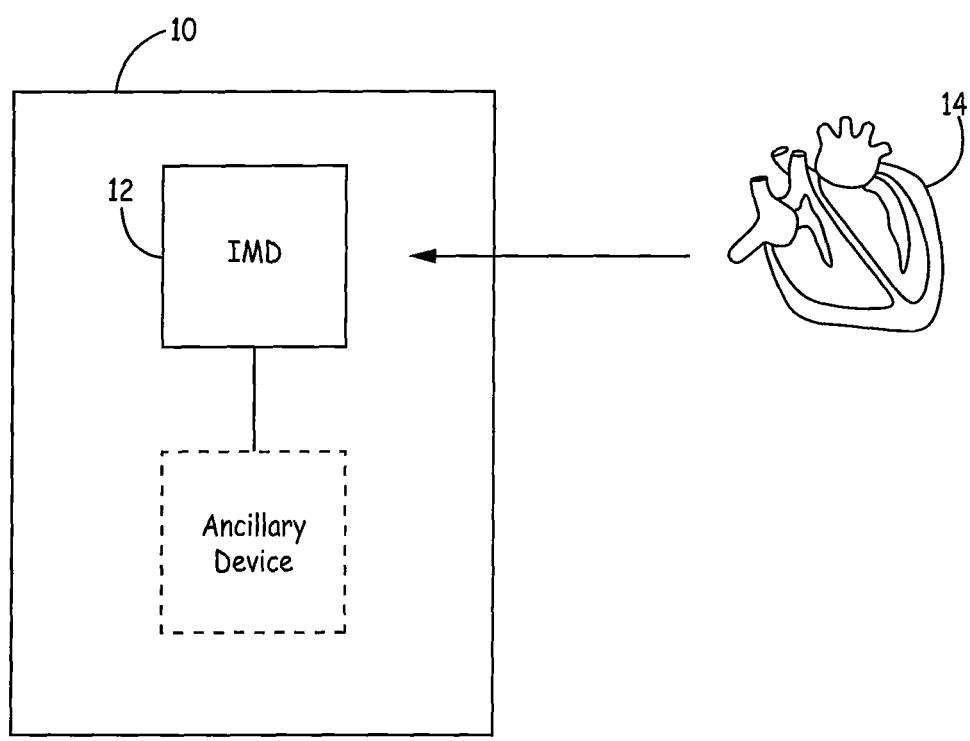
FIG. 1 is a block diagram of a system 10 for determining a risk of ventricular arrhythmia of a patient.

FIG. 1 is a block diagram of a system 10 for determining a risk of ventricular arrhythmia of a patient. An implantable medical device 12 receives EGM/ECG data from heart 14 of the patient as well as data related to the autonomic nervous system of the patient. System 10, either solely with implantable medical device 12 or in conjunction with an ancillary device, which may be either implanted or external, then calculates the risk of ventricular arrhythmia.

An exemplary example of the numeric determination of the risk found by determining the ratio QRS-Width/DFAlpha1 follows.

Eight (8) memory areas are prepared of length 4, 5, 6, 7, 8, 9, 10 and 11 in a way that area_4 has space for 4 values, area_5 for 5 values and so on.

Figure 2:
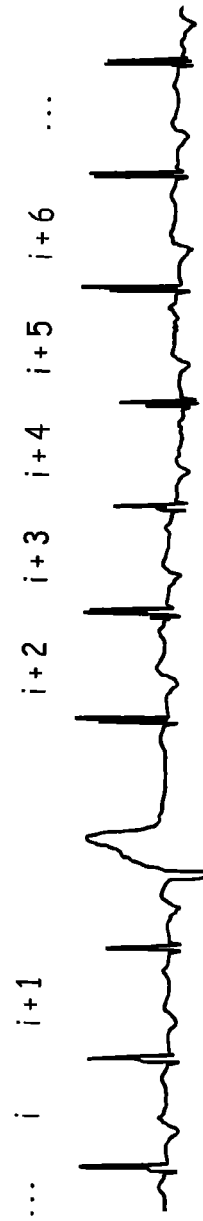
FIG. 2 is an illustration of a waveform used to calculate the intervals between two subsequent heartbeat events.

Every day for a period of twenty-four (24) hours and restarted after the twenty-four (24) hour period is completed, the following steps are performed:
- a. Derive from EGM signal the timing of heartbeat events and calculate the intervals between two subsequent heartbeat events (see FIG. 2).
- b. If an interval was derived from two normal heartbeat events, store the value of the interval (see in FIG. 2 that the two intervals around the extra beat are not stored).
- c. If the interval is a normal beat-to-beat interval do:
  - i. Store the value in the areas area_4, area_5, . . . area_11 and add to this value the value stored in the previous place in this area (calculate the cumulative sum of all previous stored values and the current value). If an area is empty, just store the value.
  - ii. If an area is completely filled then:
    1. De-trend the stored values by (1) determining the linear regression line from the stored values and (2) subtracting this line.
    2. Then get the RMS (root mean square) value of these values and add it to the specific area-sum and increment the specific area-sum-counter by one (e.g. when area_4 was processed, add the value to area_sum_4 and increment area_sum_counter_4 by one).
    3. Then "remove" the values from the area and re-start the collection of intervals for this area.
- d. In a period of no activity (e.g. at around 2 am or activity-sensor signal below a certain threshold) collect the EGM data for several (e.g. 200) normal heartbeat events and derive from the collected heartbeat events a representative heartbeat.

After collecting intervals for 24 hours, the de-trended fluctuation parameter DFAlpha1 is calculated by:
- a. Calculate the mean value of the area-sum values area_sum_4, . . . area_sum_11.
- b. Then calculate the slope of the regression line of the mean area-sum values using the logarithm of the area size (on the x-axis) and the logarithm of the corresponding mean area-sum (on the y-axis). Store the slope in DFAlpha1.

Figure 3:
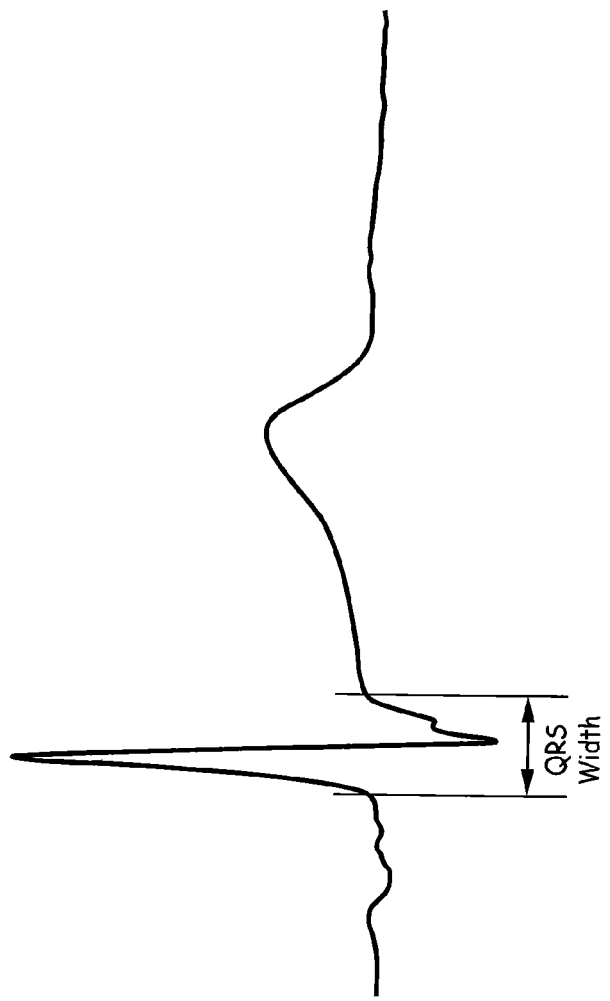
FIG. 3 is a waveform of a representative heartbeat used to derive the width of the QRS complex.

From the representative heartbeat derive the width of the QRS complex (see FIG. 3) and store the value in QRS-Width.

Calculate the ration QRS-Width/DFAlpha1 and store the result in Score.

If the score value Score is greater or equal to 135, activate the flag to 1 otherwise to 0. If the flag is set, an action is taken based on the flag.

Generally, a higher score of the local conduction system is indicative of a greater risk of a potentially near fatal ventricular arrhythmia. Generally, a lower score of the global autonomic nervous system is indicative of a greater risk of a potentially near fatal ventricular arrhythmia.

In an embodiment, if the flag is set, an alarm, e.g., an audible, tactile, visual or other sensory alarm, is activated.

In an embodiment, if the flag is set, a therapeutic action is taken with respect to the patient. For example, if the patient already has an implantable cardioversion defibrillator or a pacemaker appropriate therapies may be commenced or modified appropriate to the patient and appropriate to the risk. Alternatively or in addition, an implantable medical device, e.g., an implantable cardioversion defibrillator or a pacemaker may be implanted in the patient and programmed appropriate to the patient and appropriate to the risk.

It is to be recognized and understood that while QRS-width has been utilized herein, that other parameters of the local conduction system of the patient could also be utilized, either instead of or in addition to QRS-width. If QRS-width is used, QRS-width may be scored in time and, in particular, in milliseconds.

It is also to be recognized and understood that while a detrended fluctuation analysis slope Alpha-1 (DFa1) has been utilized herein, that other parameters of the global autonomic system of the patient could also be utilized, either instead of or in addition to the detrended fluctuation analysis slope Alpha-1 (DFa1).

In an embodiment, the period of time over which both the parameter indicative of a local conduction system of the heart of the patient and the parameter indicative of the global autonomic nervous system of the patient are measured is at least ten (10) hours.

Figure 4:
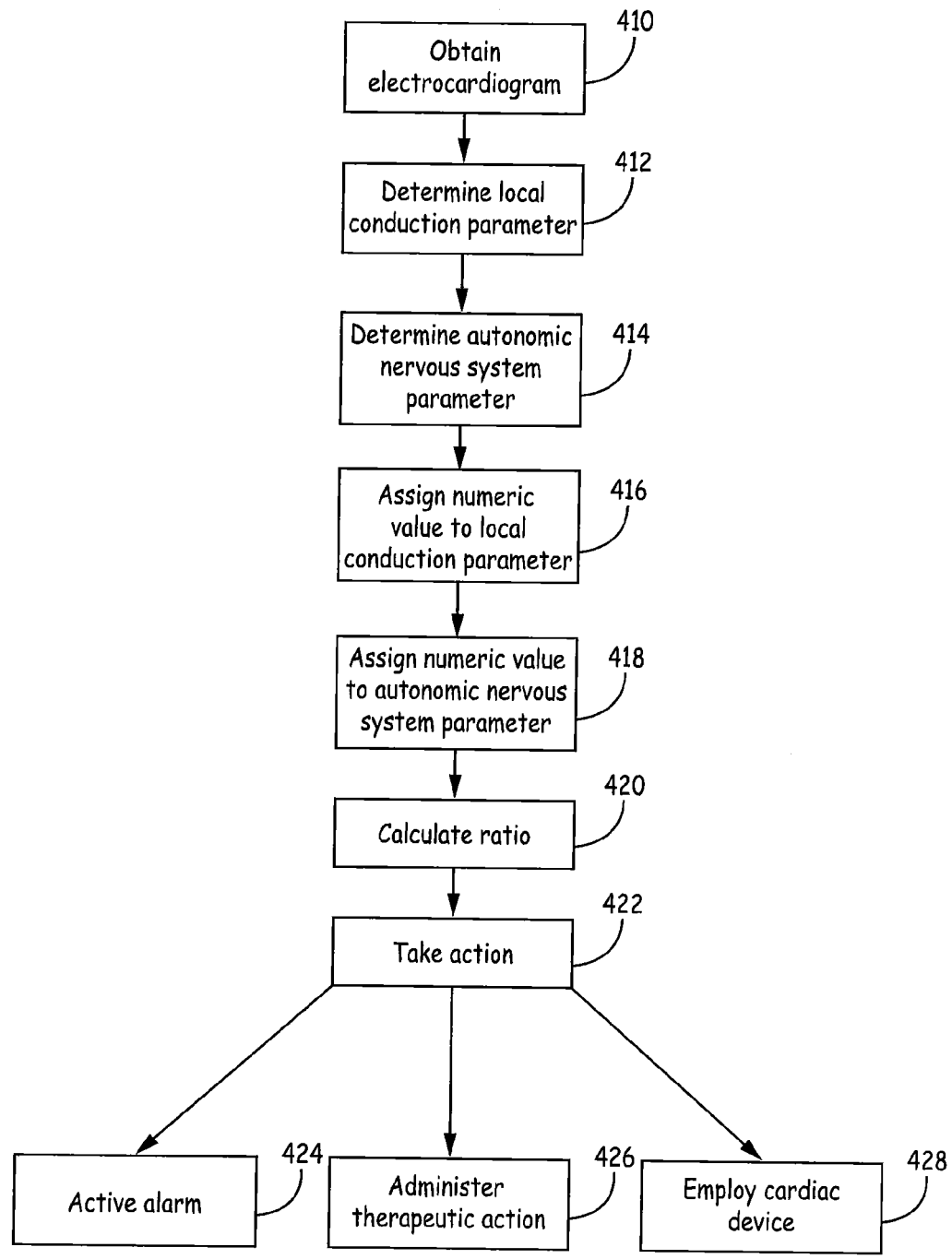
FIG. 4 is a flow chart of an embodiment.

FIG. 4 is a flow chart of an embodiment. A medical device is implanted in the patient and configured to obtain 410 an electrocardiogram of a heart of the patient. A parameter is measured 412, using the electrocardiogram, indicative of the local conduction system of the patient. A parameter is measured 414, using the electrocardiogram, indicative of an autonomic nervous system of the patient. A numeric score is assigned 416 for the parameter indicative of the conduction system of the heart of the patient. A numeric score is assigned 418 for the parameter indicative of the autonomic nervous system of the patient. A ratio of the numeric score of the parameter indicative of the conduction system of the heart of the patient and the numeric score of the parameter indicative of the autonomic nervous system of the patient is calculated 420. The risk of the potentially near fatal ventricular arrhythmia of the patient is determined to be significant if the ratio is greater than a predetermined threshold. An action responsive to the determining step is taken 422. In an embodiment, an alarm is activated 424. In an embodiment, a therapeutic action with the patient is administered 426. In an embodiment, a cardiac device is implanted 428 and operatively coupled to the medical device. The cardiac device is configured to perform a therapeutic action for the patient in response to the risk of the potentially near fatal ventricular arrhythmia. In an embodiment, the cardiac device is a cardiac pacemaker. In an embodiment, the medical device is at least one of a cardioverter and a cardiac rhythm therapy device.

Thus, embodiments of the invention are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A system for determining a risk of a potentially near fatal ventricular arrhythmia of a patient, comprising:
   an implantable medical device configured to:
     obtain an electrocardiogram of a heart of said patient;
     measure, using said electrocardiogram, a parameter indicative of a local conduction system of said heart of said patient;
     measure, using said electrocardiogram, a parameter indicative of a global autonomic nervous system of said patient;
   said system being configured to:
     assign a numeric score for said parameter indicative of said local conduction system of said heart of said patient;
     assign a numeric score of said parameter indicative of said global autonomic nervous system of said patient;
     calculate a ratio of said numeric score of said parameter indicative of said local conduction system of said heart of said patient with said numeric score of said parameter indicative of said global autonomic nervous system of said patient;
     take an action responsive to said risk of said potentially near fatal ventricular arrhythmia of said patient being significant if said ratio is greater than a predetermined threshold.

2. A system as in claim 1 wherein said action comprises activating an alarm.

3. A system as in claim 1 wherein said action comprises administering a therapeutic action with said patient.

4. A system as in claim 3 further comprising cardiac device, operatively coupled to said medical device and configured to perform a therapeutic action for said patient in response to said risk of said potentially near fatal ventricular arrhythmia.

5. A system as in claim 4 wherein said cardiac device comprises a cardiac pacemaker.

6. A system as in claim 4 wherein said cardiac device comprises a cardioverter.

7. A system as in claim 1 wherein said parameter indicative of a local conduction system of said heart of said patient comprises a QRS-width.

8. A system as in claim 7 wherein said numeric score of said QRS-width is scored in time.

9. A system as in claim 8 wherein said numeric score of said QRS-width is scored in milliseconds.

10. A system as in claim 7 wherein said parameter indicative of said global autonomic nervous system comprises a detrended fluctuation analysis slope Alpha-1 (DFa1).

11. A system as in claim 10 wherein said period of time is at least ten hours.

12. A system as in claim 10 wherein a higher value of said numeric score for said parameter indicative of said local conduction system of said heart of said patient is indicative of a greater risk of said potentially near fatal ventricular arrhythmia of said patient.

13. A system as in claim 12 wherein a lower value of said parameter indicative of said global autonomic nervous system of said patient is indicative of a greater risk of said potentially near fatal ventricular arrhythmia of said patient.

14. A system as in claim 13 wherein said numeric score of said detrended fluctuation analysis slope Alpha-1 (DFa1) is scored in slope value.

15. A system as in claim 14 wherein said parameter indicative of a local conduction system of said heart and said parameter indicative of a global autonomic nervous system of said patient step are both measured over a period of time.

16. A system as in claim 15 wherein said threshold indicative of said risk of said potentially near fatal ventricular arrhythmia of said patient is one hundred thirty-five (135).

17. A system as in claim 1 wherein said patient comprises a post myocardial infarction patient.

18. A device implemented method of determining a risk of a potentially near fatal ventricular arrhythmia of a patient, comprising the steps of:
   implanting a device in said patient configured to obtain an electrocardiogram of a heart of said patient;
   measuring, using said electrocardiogram, a parameter indicative of a local conduction system of said heart of said patient;
   measuring, using said electrocardiogram, a parameter indicative of a global autonomic nervous system of said patient;
   assigning a numeric score for said parameter indicative of said local conduction system of said heart of said patient;
   assigning a numeric score of said parameter indicative of said global autonomic nervous system of said patient;
   calculating a ratio of said numeric score of said parameter indicative of said local conduction system of said heart of said patient with said numeric score of said parameter indicative of said global autonomic nervous system of said patient;
   determining that said risk of said potentially near fatal ventricular arrhythmia of said patient is significant if said ratio is greater than a predetermined threshold; and
   taking an action responsive to said determining step.

19. A method as in claim 18 wherein said taking an action step comprises activating an alarm.

20. A method as in claim 18 wherein said taking an action step comprises administering a therapeutic action with said patient.

21. A method as in claim 20 wherein said taking an action step comprises implanting a medical device configured to perform a therapeutic action for said patient.

22. A method as in claim 21 wherein said medical device comprises a cardiac pacemaker.

23. A method as in claim 21 wherein said medical device comprises a cardioverter.

24. A method as in claim 18 wherein said parameter indicative of a local conduction system of said heart of said patient comprises a QRS-width.

25. A method as in claim 24 wherein said numeric score of said QRS-width is scored in time.

26. A method as in claim 25 wherein said numeric score of said QRS-width is scored in milliseconds.

27. A method as in claim 24 wherein said parameter indicative of said global autonomic nervous system comprises a detrended fluctuation analysis slope Alpha-1 (DFa1).

28. A method as in claim 18 wherein said period of time is at least ten hours.

29. A method as in claim 28 wherein a higher value of said numeric score for said parameter indicative of said local conduction system of said heart of said patient is indicative of a greater risk of said potentially near fatal ventricular arrhythmia of said patient.

30. A method as in claim 29 wherein a lower value of said parameter indicative of said global autonomic nervous system of said patient is indicative of a greater risk of said potentially near fatal ventricular arrhythmia of said patient.

31. A method as in claim 30 wherein said numeric score of said detrended fluctuation analysis slope Alpha-1 (DFa1) is scored in slope value.

32. A method as in claim 31 wherein said measuring a parameter indicative of a local conduction system of said heart of said patient step and said measuring a parameter indicative of a global autonomic nervous system of said patient step are both conducted over a period of time.

33. A method as in claim 32 wherein said threshold indicative of said risk of said potentially near fatal ventricular arrhythmia of said patient is one hundred thirty-five (135).

34. A method as in claim 18 wherein said patient comprises a post myocardial infarction patient.

* * * * *